(12) United States Patent
Peterchev et al.

(10) Patent No.: US 8,801,589 B2
(45) Date of Patent: Aug. 12, 2014

(54) METHODS, APPARATUS, AND SYSTEMS FOR MAGNETIC STIMULATION

(75) Inventors: Angel Vladimirov Peterchev, New York, NY (US); Sarah Hollingsworth Lisanby, New York, NY (US); Zhi-De Deng, Brooklyn, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 386 days.

(21) Appl. No.: 13/056,914

(22) PCT Filed: Aug. 4, 2009

(86) PCT No.: PCT/US2009/052768
§ 371 (c)(1),
(2), (4) Date: Mar. 9, 2011

(87) PCT Pub. No.: WO2010/017249
PCT Pub. Date: Feb. 11, 2010

(65) Prior Publication Data
US 2011/0184223 A1  Jul. 28, 2011

Related U.S. Application Data

(60) Provisional application No. 61/086,080, filed on Aug. 4, 2008, provisional application No. 61/117,858, filed on Nov. 25, 2008.

(51) Int. Cl.
*A61N 1/00* (2006.01)
(52) U.S. Cl.
USPC ................................. 600/15; 600/13; 600/14
(58) Field of Classification Search
CPC ................................. A61N 2/02; A61N 2/006
USPC ............................................ 600/9, 13, 14, 15
See application file for complete search history.

(56) References Cited

U.S. PATENT DOCUMENTS

| | | | | |
|---|---|---|---|---|
| 1,164,356 | A * | 12/1915 | Kaiser | 335/297 |
| 3,762,396 | A | 10/1973 | Ballentine et al. | |
| 4,638,798 | A * | 1/1987 | Shelden et al. | 606/130 |
| 4,832,051 | A | 5/1989 | Jarvik et al. | |
| 5,047,005 | A * | 9/1991 | Cadwell | 600/13 |
| 5,078,674 | A * | 1/1992 | Cadwell | 600/13 |
| 5,116,304 | A * | 5/1992 | Cadwell | 600/13 |
| 2007/0250139 | A1 | 10/2007 | Kanzlus | |
| 2007/0260107 | A1 | 11/2007 | Mishelevich et al. | |

FOREIGN PATENT DOCUMENTS

WO  WO 02/085449 A2  10/2002

OTHER PUBLICATIONS

Roth et al., A Coil Design for Transcranial Magnetic Stimulation of Deep Brain Regions, Journal of Clinical Neurophysiology, 19(4):361-370, (2002).*

* cited by examiner

*Primary Examiner* — Jacqueline Cheng
*Assistant Examiner* — Kaylee Wilson
(74) *Attorney, Agent, or Firm* — Mark A. Catan; Miles & Stockbridge P.C.

(57) ABSTRACT

A coil suitable for tissue stimulation and especially for transcranial magnetic stimulation (TMS) may be used in conjunction with a pulse generator to induce electric field in the brain with less attenuation in depth compared to existing TMS coils. In an example, a coil winding is formed in a solenoid configuration around the head. Various related features, methods, and embodiments are described.

16 Claims, 3 Drawing Sheets ional Application No. 61/117,858,
METHODS, APPARATUS, AND SYSTEMS FOR MAGNETIC STIMULATION

CROSS REFERENCE TO RELATED APPLICATIONS

The present application is a national stage application of International Application No. PCT/US2009/052768, filed Aug. 4, 2009, which claims the benefit of and priority to U.S. Provisional Application No. 61/086,080, filed Aug. 4, 2008, expired, and U.S. Provisional Application No. 61/117,858, filed on Nov. 25, 2008, expired, both of which are hereby incorporated by reference in their entireties herein. In the event of a conflict between the teachings of the application and those of the incorporated documents, the teachings of the present application control.

This invention was made with government support under Faculty Development Award awarded by New York State Office of Science, Technology, and Academic Research. The government has certain rights in the invention.

BACKGROUND

Transcranial magnetic stimulation (TMS) can be used to alter the function of the cerebral cortex without surgery or direct application of electrical voltages. Magnetic fields may be generated by large current pulses in strong magnets arranged close to the head of a subject. Studies have indicated that TMS is useful both therapeutically and for research into brain function.

SUMMARY

A coil suitable for transcranial magnetic stimulation (TMS) may be used in conjunction with a TMS device to induce an electric field in the brain with less attenuation in depth compared to existing TMS coils. In an example, a coil winding is formed around the head. Various related features, methods, and embodiments are described.

BRIEF DESCRIPTION OF THE DRAWINGS

The accompanying drawings, which are incorporated and constitute part of this disclosure, illustrate preferred embodiments of the invention and serve to explain the principles of the invention.

DETAILED DESCRIPTION OF THE DRAWINGS

Figure 1A:
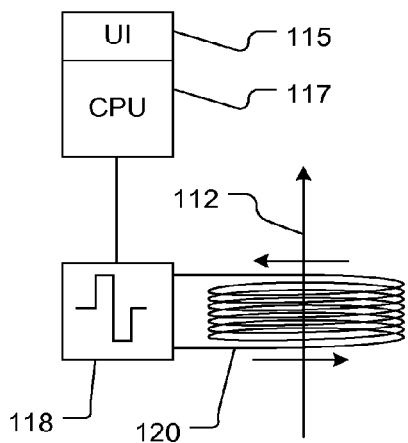
FIG. 1A illustrates a crown coil winding according to embodiments of the disclosed subject matter.

Referring to FIGS. 1A, 1B, 2A, and 2B, a coil suitable for transcranial magnetic stimulation (TMS) may be used in conjunction with a TMS device to induce electric field in the brain with less attenuation in depth compared to existing TMS coils. According to embodiments, a time-varying current is established in an air core coil winding 120 by a pulse generator 118 to create one or more magnetic field pulses. The winding 120 has an axis 112. The winding may be potted and/or wrapped around a support to control the winding 120 during energization and permit the winding 120 to be insulated and supported on the head 200 of a patient or research subject 108. The winding 120 may be merely insulated also. The supported winding 120 structure is indicated as a crown coil device at 106. The crown coil device 106 may be further supported on a wearable appliance such as a helmet 104.

In the illustrated example, the crown coil device 106 is formed such that the winding 120 wraps around the head and can be oriented such that the axis 112 of the winding 120 is directed as desired. For example the crown coil device 106 can be positioned and oriented around the perimeter of the head as a crown. The crown coil 106 induces a circular electric field in the transverse plane of the head, with lateromedial orientation in frontal cortex. The crown coil device 106 winding 120 may include any number of turns. Also, the crown coil device 106 may include multiple windings to produce a similar effect as will be clear from the further description of the properties of the device and the variations thereon.

Figure 1B:
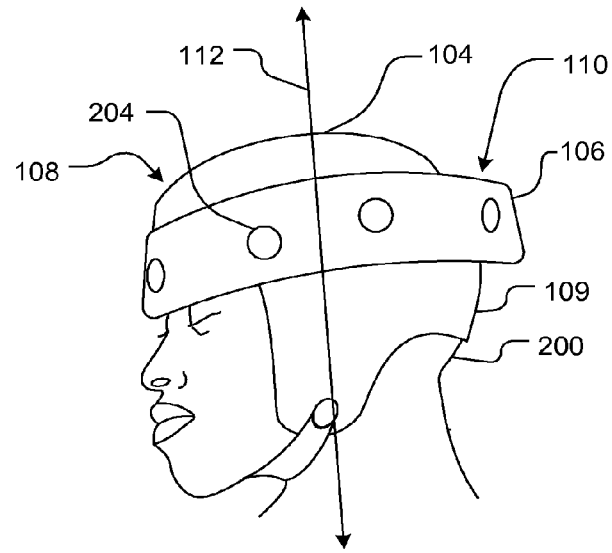
FIG. 1B is an illustration of a crown coil device according to embodiments of the disclosed subject matter.
Figure 2A:
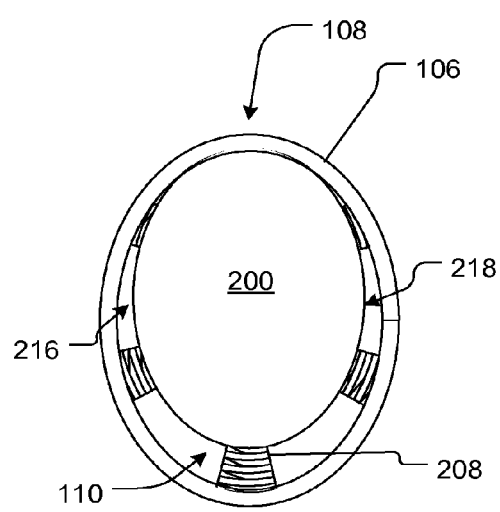
FIG. 2A is a section view of a crown coil device worn on a head with spacers to adjust the spacing according to embodiments of the disclosed subject matter.
Figure 2B:
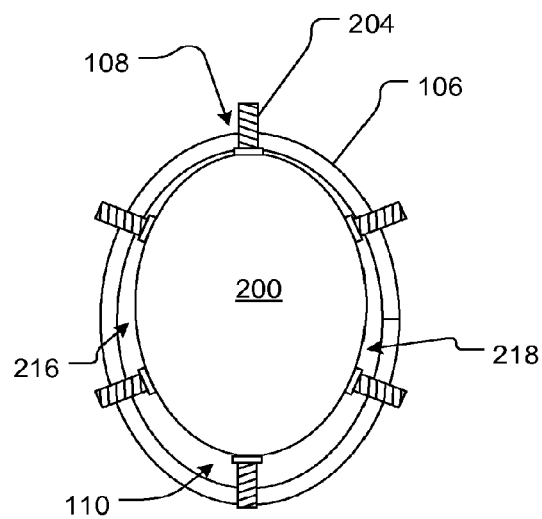
FIG. 2B is a section view of a crown coil device worn on a head with adjustable spacers (adjustors) to adjust the spacing according to embodiments of the disclosed subject matter.

In the example illustrated in FIGS. 1B, 2A, and 2B, an anterior portion 108 of the crown coil device 106 lies directly over the forehead as indicated at 108 and is spaced from the occipital area 110 and temporal areas 216, 218 of the head 200. Thus, the illustrated configuration may create a stronger stimulation of frontal brain structures, such as the frontal pole, and medial frontal and orbito-frontal cortices, than occipital structures. The crown coil device 106 may also be suitable for direct or indirect stimulation of the subgenual anterior cingulate cortex (sACC) which is a deep brain structure playing a central role in the brain circuits associated with major depression and other psychiatric disorders. Besides the targeted frontal cortex, lateral and posterior brain regions will be stimulated as well.

In embodiments, the crown coil device 106 is larger than the head of the patient (or test subject) 106 and is spaced from the head at the posterior as indicated at 110, thereby focusing energy at the frontal lobe. Focusing of the electric field in the frontal lobe may be enhanced by introducing one or more spacers 204 or 208 to distance the windings from the head laterally 216, 218 and posteriorly 110. An example of this approach is illustrated where the coil is mounted on a helmet 109 so as to provide spacing between the head 200 and the crown coil device 106, or more specifically, the winding 120 therein, except over the forehead, where the winding 120 lies directly over the skin/scalp. As shown in FIG. 2, a therapeutic or experimental coil 206 has spacing elements 204, 208 to vary the spacing of the coil 206 at various points around the head.

The embodiment of FIG. 2A shows spacers 208 of various thicknesses which may be provided in a kit and used in different combinations and placements to position and fit the crown coil device 105 as desired. For example, the spacers may be elastomeric pads, blocks that fit between a liner and the helmet, or that fit between the crown coil and the helmet 109 of the crown coil device 106. The spacers 208 can be moved to different locations or be of any desired design, for example, to permit the coil to directly overlie the head at any desired point. As illustrated in the embodiment of FIG. 2B, alternatively the coil can be supported by a positioning device with respect to which the patient's head is stably positioned and oriented. For example, illustrated are adjustors 204 whose depth relative to the crown coil device 106 can be changed to position the head 200 relative to the crown coil device 106. The drawing illustrates screw-type adjustors but any suitable arrangement could be used, for example, the spacers may be fixed or adjustable. The illustration is figurative and not restrictive, since many different mechanisms could be employed. Note also that the head 200 may be supported by a fixture that is different from the crown coil device 106 altogether. For example, it may be supported on a movable arm as is a diagnostic x-ray emitter or positioned by a robot or 3-axis positioning table (not shown).

To provide for further variation in head sizes and treatments, multiple coils may be provided in a kit with different sizes and shapes along with a kit of spacers to provide for positioning. So, for example, the coil need not mimic the shape of the head, for example.

Figure 3:
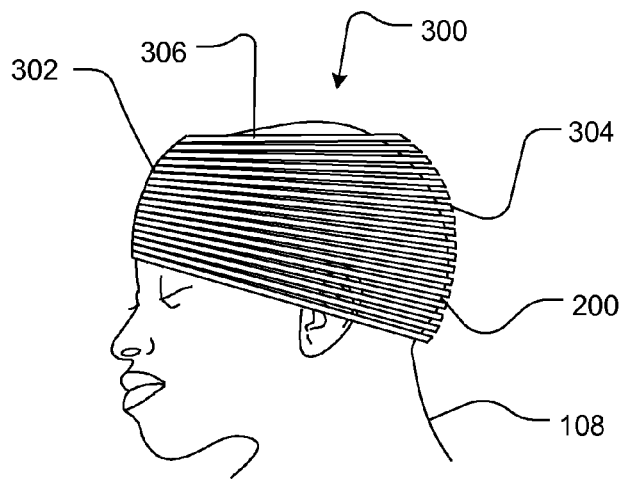
FIG. 3 shows a fanned configuration of a crown coil according to embodiments of the disclosed subject matter.

FIG. 3 illustrates an alternative variation of a crown coil 300 that has the turns 306 spread out in one part of the head as indicated at 304 and close together in a different part of the head as indicated at 302. In an embodiment, the fanned coil 300 and/or a support therefor, is configured to permit adjustment of the degree of fanning. For example, an adjustable support (not shown) may be incorporated in a support mounted on a helmet. However, because the turns are preferably held very stably due to strong magnetic field the adjustment device may need to be heavy and therefore may not be desirable. An alternative way to allow a treatment professional to employ a coil with degrees of spacing between windings and different locations of the closely-spaced and tightly-spaced windings is to provide a set of differently shaped coils with varied degrees of fanning at different locations and different shapes. In such embodiments, the windings may be encapsulated or potted in a strong light weight polymer. In another embodiment, the coils of all of the embodiments may be provided in multiple parts to allow custom fitting to the heads of the patients. Electrical and mechanical interconnections would be provided for by any suitable devices and techniques.

The fanning of the windings toward the rear side of the patient, as illustrated in FIG. 3, helps to focus the electric field in the frontal lobe and reduce the field strength at other sites, for example, the occipital cortex and the lateral regions of the head. In a typical implementation of the coil winding of any of the disclosed embodiments, high-current copper wire with high-voltage insulation may be used. The winding is preferably connected to a high-voltage, high-current cable terminated in a connector, similar to those of conventional TMS coils, which allow the coil to be connected to a TMS device which delivers electric current pulses with peak current up to 10 kA. The coil can be mounted on a helmet, or fixed with respect to the head with a coil holder device, or held by an external support over the subject's head.

The term "crown coil" is used here to identify all windings that run around the head, not only to coils that lie where a traditional crown or hat might be worn. For example, a crown coil may be positioned such that it lies in a circle in roughly the coronal plane, running under the chin or behind the head and over the top of the head.

The windings of the crown coil may encircle the head in an example configuration as shown in the drawings. The windings may be wound in a solenoidal (helical) arrangement or in a radially stacked, or other arrangement. Distancing portions of the winding from the head or spreading the wire turns (fanning) to reduce stimulation strength away from the target may be achieved through appropriate configuration of the crown coil as discussed above. Preferably, the windings may cover the forehead to target frontal structures.

Preferred uses of the crown coil configuration include:
1) direct stimulation of deep brain structures (<5 cm depth) that are beyond the reach of traditional coils,
2) indirect stimulation of even deeper or more remote targets (>5 cm depth) that are transsynaptically connected to the regions directly stimulated,
3) stimulation of (directly or indirectly) deep regions of the prefrontal cortex,
4) stimulation of (directly or indirectly) deep regions of the occipital cortex,
5) simultaneously and synchronously stimulating (directly and indirectly) deep regions of the right and left hemispheres, and
6) asymmetric brain stimulation.

The above list is illustrative of examples and not limiting of the uses to which the crown coil configuration may be put.

A crown coil device according to any of the embodiments may incorporate elements that provide an electronically switchable "sham" mode, which recreates ancillary effects of TMS such as clicking, vibration, and scalp stimulation, without significant stimulation of the brain. Sham mode may be used for double-blind studies to test therapeutic effectiveness and to control for ancillary effects in neuroscience studies. Each of the above features expands the utility of TMS as a tool to study and treat neurological and psychiatric disorders.

Lower attenuation in depth, and concomitant increased depth of effective stimulation, may be used for research and therapeutic applications that take advantage of the ability to stimulate deeper brain structures and/or larger total stimulated brain volume. Many brain targets of interest for basic neuroscience research, preclinical research, pathophysiology research, and therapeutic applications in neurology and psychiatry lie deep in the brain. An increased depth of effective stimulation will increase the range of targets that are accessible to direct stimulation, and will expand the number of still deeper targets that could be reached transsynaptically.

The crown coil configuration additionally provides bilateral simultaneous stimulation of the prefrontal cortex (with the anterior positioning of the coil) or the occipital cortex (with the posterior positioning of the coil). Simultaneous stimulation of deep regions of the left and right hemisphere may be used to facilitate the study of the functional role of the prefrontal and occipital cortices in behaviors, cognitive functions and sensory processing that are bilaterally represented. It may also be used to facilitate the treatment of neurological and psychiatric disorders that involve bilateral regions of prefrontal or occipital cortices. The crown coil configuration may be used for bilateral simultaneous deep prefrontal or occipital stimulation preferably using a single coil and a single TMS stimulating device.

Finally, the crown coil may permit the use of less energy than conventional coils to stimulate deep brain regions. For example, the crown coil may use less than one third of the energy a conventional Magstim double-cone coil to stimulate structures at 6 cm in depth. Larger coils, such as the crown coil, can provide slower diminution of field strength with depth and also can stimulate a larger brain volume. These factors may have therapeutic benefits.

Examples of therapeutic applications of the crown coil in psychiatry include treatment of major depressive episodes in the context of unipolar major depressive disorder or bipolar disorder (sample deep targets include subgenual anterior cingulate cortex and medial prefrontal cortex), obsessive compulsive disorder (e.g., orbitofrontal cortex and anterior cingulate), schizophrenia (e.g., ventral striatum, hippocampus and thalamus), substance use disorders (e.g., insula and orbitofrontal cortex), impulse control disorders (e.g., orbitofrontal cortex), and suicide prevention (e.g., orbitofrontal cortex, other depression targets). Examples of therapeutic applications in neurology include movement disorders such as Parkinson's disease, essential tremor, Tourette's, dystonia (e.g., thalamus, basal ganglia), and epilepsy (various targets).

The dorsolateral prefrontal cortex has been the most common target in the treatment of major depression, although depression is associated with dysregulation in a wider cortical-subcortical-limbic network. The subgenual anterior cingulate cortex (sACC) may be central to this network, and deep-brain stimulation (DBS) with chronically implanted electrodes in the white matter underlying the sACC has a demonstrated strong antidepressant effects in promising initial studies. Other therapeutic targets for depression include the ventral portion of the anterior limb of the internal capsule and adjacent dorsal ventral striatum, nucleus accumbens and habentila. Since the majority of these brain areas are not superficial, accessing them with TMS require coil designs suitable for stimulation in depth. For example, the sACC and the nucleus accumbens lie at depths of approximately 6 and 7 cm, respectively. These deep-brain regions may be modulated transsynaptically by stimulating more superficial nodes of the network. For example, the orbitofrontal and medial frontal cortices, and the frontal pole lie at depths of 3 to 4 cm and have strong connectivity to anterior cingulate cortex, and, therefore, could be promising targets.

Simultaneous bilateral deep prefrontal cortical stimulation using the crown coil may also have therapeutic applications in major depression, as bilateral prefrontal stimulation may be more effective than unilateral stimulation in the treatment of depression. Furthermore, bilateral prefrontal stimulation may be used to achieve results similar to electroconvulsive therapy (ECT), which is currently the most powerful antidepressant available. By using a coil that delivers simultaneous low frequency stimulation to large regions of bilateral frontal and prefrontal structures, similar results to ECT may be achieved, but without inducing a seizure, thereby avoiding major side effects associated with ECT (e.g., amnesia resulting from a seizure).

In addition to subconvulsive applications of TMS, the crown coil may also improve the efficacy of magnetic seizure therapy (MST), a convulsive version of TMS which is a less invasive alternative to ECT for treatment-refractory depression. MST utilizes the relative focality of magnetic induction of electrical currents in the brain instead of the transcranial application of electricity utilized in ECT. However, conventional MST has suffered from major technology bottlenecks, including excessive heating and energy consumption. By using a crown coil, the penetration depth of the electric field may be extended thereby enabling more effective seizure induction in frontal regions, while reducing the amount of energy necessary to produce a desired electric field strength in the brain. This reduced energy requirement thereby results in less heating. Thus, the crown coil can be used to significant advantage in MST.

Repetitive TMS (rTMS) may have the ability to produce lasting changes in neuronal activity that persists beyond the period of stimulation. Such ability may confer therapeutic potential for psychiatric and neurological disorders. Efficacy of rTMS may be enhanced through optimization of rTMS dosing. For example, increased pulse intensity has been associated with improved antidepressant efficacy. Increasing intensity results in greater depth of penetration.

The dorsolateral prefrontal cortex has been the most common target in depression, although major depression is associated with dysregulation in a wider cortical-subcortical-limbic network. The subgenual anterior cingulate cortex (sACC) may be central to this network. Deep-brain stimulation (DBS) with chronically implanted electrodes in the white matter underlying the sACC has been shown to have a strong antidepressant effect. Other brain targets for depression may include the ventral portion of the anterior limb of the internal capsule and adjacent dorsal ventral striatum, nucleus accumbens and habenula. Therefore these targets within this distributed network may be treated using the crown coil devices described herein. These deep-brain regions might also be modulated trans-synaptically by stimulating more superficial nodes of the network. For example, the orbitofrontal and medial frontal cortices and the frontal pole lie at depths of 3 to 4 cm and have strong connectivity to anterior cingulate cortex, and, therefore, may be promising targets.

Additionally, the crown coil could be used for basic neuroscience research as well as for therapy. For example, the crown coil could be used to stimulate the occipital lobe for studies of the visual system. To accomplish this, the crown coil may be rotated in the horizontal plane so that the anterior portion of the coil winding lies over the occipital lobe for visual cortex stimulation or shift it to bring it closer to the head in the area desired to be stimulated. Human visual perception may be suppressed by magnetic stimulation over the visual cortex. The topography of the visual cortex and the mechanisms of visual perception may be explored by deep-brain stimulation of the occipital lobe using the crown coil. Occipital stimulation has also been studied in the treatment of blindness resulting from stroke. In particular, TMS can induce plasticity that may be helpful in post-stroke recovery. Accessing deep occipital regions with the crown coil may have therapeutic potential in this respect.

The crown coil may also be used for stimulation of peripheral nerves for the study of nerve conduction or for the treatment of pain, deep tissue stimulation for the treatment of pain, and for the stimulation of other brain areas with deep lying targets, such as the occipital cortex. The coil may be used to study and treat other disorders that are linked to neuronal circuits, which may be deep and inaccessible to conventional TMS coils. Such disorders may include, but are not limited to, substance abuse/dependence, schizophrenia, anxiety disorders, impulse control disorders, pain, movement disorders, and epilepsy.

Advantages provided by the crown coil may include non-invasive stimulation of previously inaccessible (by TMS) and potentially more effective brain targets for the treatment and study of depression as well as other psychiatric and neurological disorders.

Figure 4A:
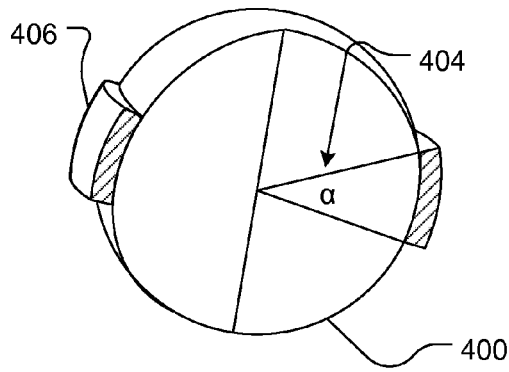
FIGS. 4A and 4B show modeled configurations of crown and C-coil TMS systems for which predictions of E-field were made.
Figure 4B:
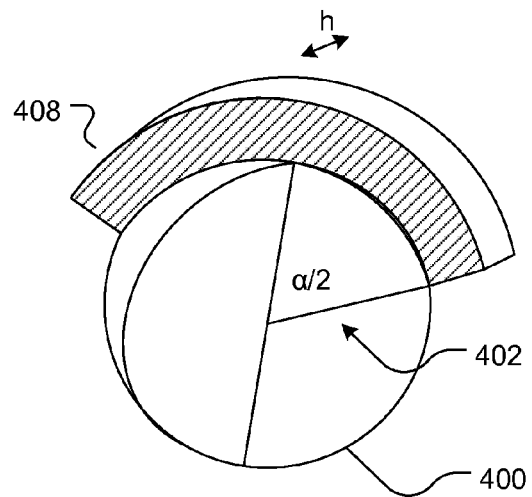

Referring to FIGS. 4A and 4B, coil and electric field modeling was performed using a 3-D electromagnetic time-harmonic solver, such as that employed in the finite element method (FEM) package MagNet (Infolytica, Inc.). The human head 400 was modeled by a multilayer conducting spherical-shell model with 8.5 cm radius, including the skin (0.5 cm thickness), skull (0.7 cm), cerebrospinal fluid (0.3 cm), gray matter (0.5 cm) and white matter (6.5 cm), with suitable dielectric properties such as described in "Three-dimensional head model simulation of transcranial magnetic stimulation," IEEE Trans Biomed Eng, vol. 51, pp. 1586-1598, 2004. The electric field attenuation was calculated as a function of depth, d, by computing the maximum electric field intensity on spherical surfaces of radial distance d from the surface of the head model 400.

Figure 5A:
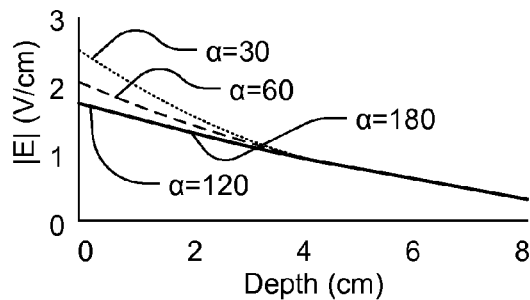
FIGS. 5A and 5B show results of modeled configurations of crown and C-coil TMS systems.

A simplified model of a "crown" coil 406 and a C-coil 408 are shown in FIGS. 4A and 4B. Referring to 5A, and 5B, data the electric field versus depth is graphed as predicted for various opening angles α (indicated at 404 for the crown coil and at 402 for the C-coil) and for a crown coil and a C-coil with the field being normalized to 1 V/cm at 4 cm depth. The spread of the winding is parameterized by angle α. As α increases, the rate of electric field attenuation decreases, as shown in FIG. 5A. As α approaches 180°, the magnetic field intensity within the sphere becomes uniform, resulting in linear electric field attenuation in depth. The latter configuration is not physically realizable for brain stimulation, but illustrates that the slowest possible rate of electric field attenuation corresponds to linear decay in depth.

In actual implementation, the anterior portion of the winding lies over the forehead, and is thus suitable for stimulation of the frontal pole, and medial frontal and orbitofrontal cortices. The crown coil induces a circular electric field in the transverse plane of the head, with latero-medial orientation in frontal cortex. Besides the targeted frontal cortex, lateral and posterior brain regions may also be stimulated. Focusing of the electric field in the frontal lobe may be improved by spreading out the windings and/or introducing a spacer to distance the windings from the head laterally and posteriorly. This may be implemented, for example, through flexible or rigid spacers or a movable spacer mechanism as discussed. Rigid spacers may be provided as a kit for fitting a patient for a desired treatment.

Figure 5B:
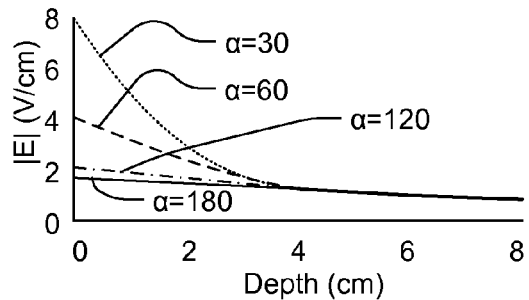

Further, a model of a C-shaped core coil is shown in FIG. 4B. The coil is wound around a ferromagnetic C-shaped core which has inner radius of 8.8 cm, outer radius of 15.8 cm, height h=7 cm, and arc-opening angle α. Simulations have shown that C-shaped coils with wide opening angle results in slower field decay with depth at the expense of reduced focality when compared to conventional ferromagnetic core figure-8 coils. A linear, homogeneous and isotropic model for the ferromagnetic core was used with relative permeability of 1000 and conductivity of 1 S/m. Similar to the crown coil, as a increases, the rate of electric field attenuation decreases and approaches a linear decay for α=180° as shown in FIG. 5B. When the C-shaped core coil is positioned to straddle the forehead, it induces a circular electric field pattern in the sagittal plane of the head, with peak field along the midline under the center of the coil. The return-current path passes through the base of the brain, which may result in undesired stimulation of the brainstem.

Increasing h and/or the outer radius of the C-core coil reduces energy, electric field attenuation in depth, and magnetic flux density in the core, which may alleviate core saturation. However, enlarging the core dimensions also reduces focality and increases the weight and cost of the coil.

Traditionally, TMS intensity may be calibrated relative to the threshold for motor cortex activation. Neuronal stimulation in the motor cortex is estimated to occur at a depth of approximately 2 cm from the surface of the scalp. Accordingly, the peak electric field strength is considered at the depth of interest relative to that at 2 cm depth. Further, scalp stimulation can be quantified by the peak electric field strength at depth of 0.25 cm relative to that in superficial cortex, that is, $\max(|E_{0.25cm}|/|E_{2cm}|)$. Focality refers to the degree of localization of the electric field induced by the TMS coil. The spatial spread of the electric field may be measured by the percentage of total brain volume (gray matter and white matter) that is exposed to electric field strong enough to induce neuronal depolarization. The larger the stimulated brain volume, the less focal the coil is. For example, if the electric field strength at the target region is 1 V/cm (representative threshold for neuronal activation with TMS,) then the ratio of the brain volume where $|E|>1$ V/cm to the total brain volume is calculated. Energy refers to the energy delivered to the coil in order to achieve a given electric field strength (e.g., 1 V/cm) at the target brain region (e.g., 6 cm).

Table 1 compares the above described figures of merit for conventional TMS coils as well as representative crown coil and C-shaped core coil designs. Clearly, the crown and C-core coils have higher electric field strengths in depth, but also induce neuronal activation in a larger volume of the brain. Note that for conventional coil designs such as the figure-8 or the circular coils, the energy required to induce threshold field strength at 6 cm depth is larger than the maximum energy most stimulators can deliver. Further, the ferromagnetic cores of the figure-8 and C-core coils would experience significant magnetic saturation far stimulation of 6 cm deep targets (Table 1). Saturation causes sharp rise of the coil current, potentially undesirably loading the coil driving circuit. Thus, air-core crown coils may be better suited for the high magnetic flux densities required for dTMS.

As shown by the data in Table 1, the crown coil induces the strongest electric field in depth with the minimum amount of energy compared to other types of TMS coils. Further, synchronous or sequential firing of TMS coil elements was used; however, synchronous firing of all coil elements may be more effective at stimulating deep neurons than sequential firing.

TABLE 1

Comparison of electric field strength in scalp (0.25 cm), superficial cortex (2 cm), and subgenual cingulate (6 cm), and locality and energy for various coil designs.

|  | $E_{6\ cm}/E_{2\ cm}$ | $E_{0.25\ cm}/E_{2\ cm}$ | Simulated vol. (%) | Energy (J) |
|---|---|---|---|---|
| Figure-8 no core | 0.13 | 2.59 | 42 | 3723 |
| Figure-8 ferro core | 0.13 | 2.18 | 39 | 851* |
| Circular 90 mm. | 0.19 | 2.07 | 57 | 1832 |
| Double cone | 0.19 | 1.88 | 50 | 454 |
| C-core coil α = 140° | 0.32 | 1.34 | 77 | 491* |
| Crown coil | 0.33 | 1.48 | 72 | 138 |

Peak |E| normalized to 1 V/cm at 6 cm depth.
*Core saturation would occur.

The figures of merit discussed with regard to Table 1 were also computed as a function of angle, α, for the crown coil and the C-core coil. The results are shown in FIGS. 6A through 6D.

Figure 6A:
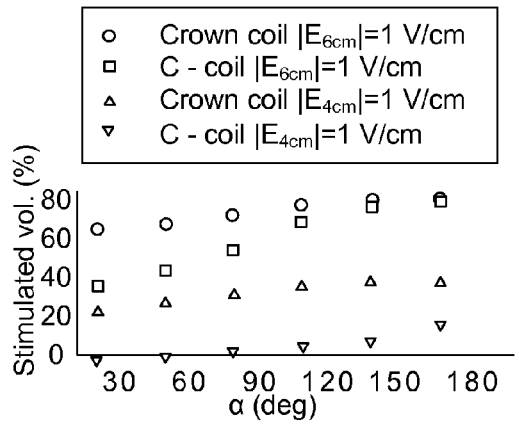
FIG. 6A is a graph showing the stimulated volume according to a simulation for C-core coil and Crown coil for |E| thresholds at depth for various opening angles.
Figure 6B:
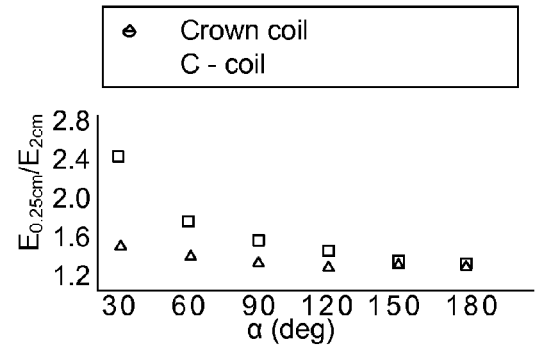
FIG. 6B is a graph showing first ratios of |E| at defined depths for various opening angles.
Figure 6C:
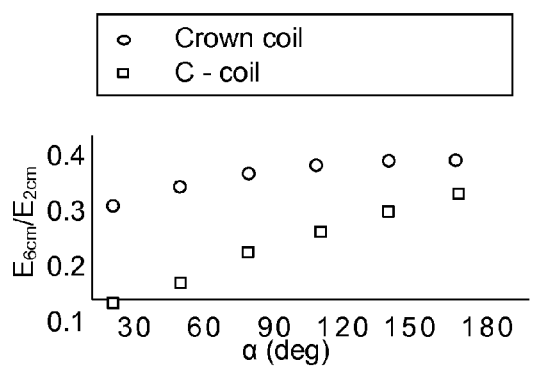
FIG. 6C is a graph showing second ratios of |E| at defined depths for various opening angles.
Figure 6D:
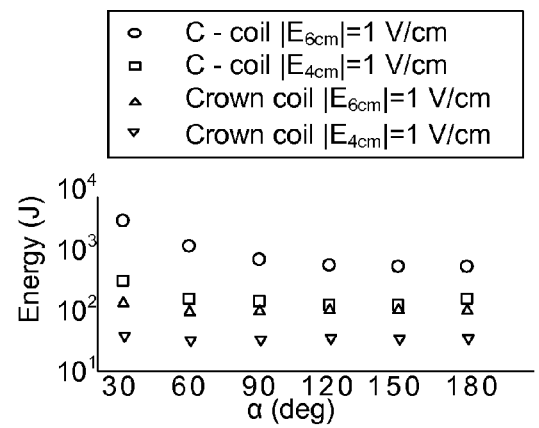
FIG. 6D is a graph showing the Energy required to achieve defined |E| thresholds at depth according to a simulation for C-core coil and Crown coils.

FIG. 6A is a graph showing the stimulated volume according to a simulation of C-core coil and Crown coil for $|E_{6cm}|=1$ (field strength at 6 cm depth) and $|E_{4cm}|=1$ (field strength at 4 cm depth) for opening angles of 30, 60, . . . 180 degrees. FIG. 6B is a graph showing first ratios of $E_{0.25cm}/E_{2cm}$ (ratio of electric field at 0.25 cm depth to that at 2 cm depth) for opening angles of 30, 60, . . . 180 degrees. FIG. 6C is a graph showing second ratios of |E| at defined depths for various opening angles of 30, 60, . . . 180 degrees. FIG. 6D is a graph showing the Energy required according to a simulation of C-core coil and Crown coil for $|E_{6cm}|=1$ (field strength at 6 cm depth) and $|E_{4cm}|=1$ (field strength at 4 cm depth) for opening angles of 30, 60, . . . 180 degrees.

Focality and energy curves were calculated for electric field strength of 1 V/cm at depth of 6 cm. Increasing the coil dimensions resulted in reduced scalp stimulation and increased electric field strength in depth, at the expense of larger stimulated brain volume (reduced focality).

Suprathreshold TMS of deep-brain structures such as sACC may pose risks of seizure or unintended neuromodulation of other brain regions. More superficial regions, such as white matter fibers and cortical areas (e.g., orbitofrontal and medial frontal cortex, and frontal pole) that project to the anterior cingulate, may be better targets for indirect stimulation of a deep target. TMS of these targets with tolerable scalp sensation and limited superficial cortex stimulation would require the use of relatively non-focal coils, such as the described crown coil or C-shaped core coil. However, as reflected in the simulated data of Table 1, the crown coil has the best overall performance for dTMS, since it has slow electric field attenuation in depth, uses less energy, and does not suffer from core saturation. Further refinements to the crown coil configuration may be employed in view of actual induced electric fields and the desired brain target or targets.

Various method and apparatus embodiments are described below. The descriptions hereinbelow are not exclusive.

A TMS coil may be configured to focus a field at a first location of the skull of a patient and spread it out at a second location of the skull of the patient, the windings being spaced further apart at the second location than the first. The windings may encircle the head. The windings may be substantially parallel to the transverse plane. The spacing of the windings may be adjustable by means of an adjustable support.

A TMS coil may be positioned on a helmet, for example and preferably, a coil whose windings encircle the head. The term helmet is used figuratively to connote a support. The windings may be parallel to the transverse plane. The helmet may be configured to allow the insulated windings to be in direct contact with the skin. The helmet may have large openings to allow air to flow around the head. The helmet may have fixed or adjustable spacers to allow the coil to be spaced from the head different distances at different locations.

Any of the above embodiments may include an adjustable sham mode to generate at least one of sounds, vibration, scalp stimulation effects. For example, actuators may be incorporated in the helmet. Alternatively, an actual treatment coil as well as an identical looking sham device may be provided as a kit.

Treatment methods using the above may include, but are not restricted to: 1) direct stimulation of deep brain structures (<5 cm depth) that are beyond the reach of traditional coils, 2) indirect stimulation of even deeper or more remote targets (>5 cm depth) that are transsynaptically connected to the regions directly stimulated, 3) stimulation of (directly or indirectly) deep regions of the prefrontal cortex, 4) stimulation of (directly or indirectly) deep regions of the occipital cortex, and 5) simultaneously and synchronously stimulating (directly and indirectly) deep regions of the right and left hemispheres.

The coil may be used to study and treat other disorders that are linked to neuronal circuits that are deep and inaccessible to conventional TMS coils, such as substance abuse/dependence, schizophrenia, anxiety disorders, impulse control disorders, pain, movement disorders, epilepsy, and others.

Treatment methods using the above may include, but are not restricted to: treatment of major depressive episodes in the context of unipolar major depressive disorder or bipolar disorder (sample deep targets include subgenual anterior cingulate cortex and medial prefrontal cortex), obsessive compulsive disorder (e.g., orbitofrontal cortex and anterior cingulate), schizophrenia (e.g., ventral striatum, hippocampus and thalamus), substance use disorders (e.g., insula and orbitofrontal cortex), impulse control disorders (e.g., orbitofrontal cortex), and suicide prevention (e.g., orbitofrontal cortex, other depression targets). Examples of therapeutic applications in neurology include movement disorders such as Parkinson's disease, essential tremor, Tourette's, dystonia (e.g., thalamus, basal ganglia), and epilepsy (various targets). Preferred methods include treatment of such disorders using a crown coil, i.e., one encircling the head.

Any of the above may be used for brain research. An example is suppressing human visual perception by magnetic stimulation over the visual cortex. In an embodiment, a coil encircling the head and overlying the occipital lobe may be used for that purpose. This structure may also be used for treatment of stroke or other impairment of the visual system.

Although coils are known for various applications, the use of certain coils for TMS is still a developing area. Described in this document is a coreless TMS coil that is configured with one or more supports to permit it to be positioned around the head of a subject or patient. The coil is configured to carry currents including one or more pulses of kiloampere magnitude. Preferably the support for the coil is strong enough to resist the forces between turns at such high current rates. So a housing or frame should be rigid and strong and capable of supporting each wind of the winding. Also, if the support includes a helmet, it may be desirable, as explained above, to arrange the helmet and winding such that the current carrying turns are as close as possible to the skin, at least at portions. So, for example, a helmet support may be cut out at locations so that the crown coil can run directly against the skin at portions. This may necessitate multiple helmets with cutout portions at different locations of the helmet to place the crown coil device against the skin at various locations. Also, spacers may be positioned to allow the crown coil to be located close to the skin. So, for example, the adjustors may be located, or locatable at positions that allow the crown coil to be placed directly against the skin at selectable or predefined locations. As described above, the coil may be free of magnetic material, that is, it may lack a core or any magnetic lens, i.e., magnetic focusing material.

Treatment and research coils configured for fitting over the head may be approximately circular or elliptical in cross section. They may also have other shapes but effectively surround the head of a subject or patient. With a maximum dimension (roughly the diameter) of 30 cm and opening angle $\alpha=30°$, the depth of the coil would be about 6 cm axial dimension (dimensional along the axis of the coil). In embodiments, the coil has an internal diameter of 15-30 cm and an axial dimension of 4-8 cm. The axial dimension may be about ⅓ to one half the internal diameter or maximum dimension, for example. Other opening angles may be used and other embodiments may have different sizes. The shape of the coil may depart from circular depending on the application, which is not necessarily related to deep brain stimulation but may be use for stimulating other tissue structures. The above dimensions are based on the size of the head.

Figure 9:
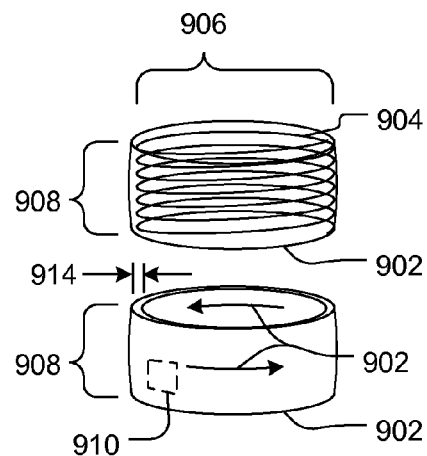
FIG. 9 is a top view of several configuration of crown coil devices according to embodiments of the disclosed subject matter.

FIG. 9 illustrates certain configuration features of crown coil devices. An axial dimension 908 of a crown coil device 902 may be, for example, approximately ⅓ to ⅔ a maximum size (e.g., diameter of a round coil) of an opening therethrough 908. In embodiments, the crown coil contains a winding which forms a solenoid which essentially refers to any windings that function substantially as a flowing sheet of current about an axis as illustrated by arrows 902 which may be accomplished by turns that are helical and run in a single direction or multiple directions. But turns may run in other patterns as well and produce the same solenoid effect. Generally such turns may form parallel (or roughly parallel) runs through arbitrary wall portions 910 of the surface of the coil device 902. The crown coil device 914 may be described as having a radial thickness or wall thickness as indicated at 914. The windings are preferably configured such that the axial dimension is substantially greater than the this wall thickness. The winding of the coil may be potted or provided with some other support that provides a sturdy unitary structure with accessible terminals for electrical attachment to an energization device.

The crown coil is preferably configured to handle peak currents of at least 1000 amperes and insulated to handle voltages of at least 1000 volts. The current may be varied to produce the electrical field in the body tissue. Frequency components of at least 100 Hz may be generated by a waveform generator. Various types of waveforms, voltages, and currents have been used for TMS. Such waveforms associated with TMS may be used in combination with the embodiments disclosed in the present specification. Pulse generators for TMS have controls that control the waveform, power, number, and timing of the pulses. Referring again to FIG. 1A, these may be provided in the form of a computer 117 with a (e.g. software) user interface 115 with software controls. The computer 117 may be a computer with a waveform generator that is electrically connected to a power circuit 118 that generates the power pulses supplied to the coil as illustrated in FIG. 1A.

The "fanned out" configuration of FIG. 3 can be embodied in a variety of configurations. For example, the turns can be uniformly distributed one side over a longer axial dimension than on an opposite side of the winding. Alternatively, turns can be grouped such that they are not uniformly distributed but cover a larger axial dimension than the other side. Turns can be arrayed in a variety of patterns, for example, to help contribute the structural integrity of the crown coil and such variations are within the scope of the disclosed embodiments. Thus, it should be clear that the windings are not limited to helical or any other particular winding pattern.

Figure 7:
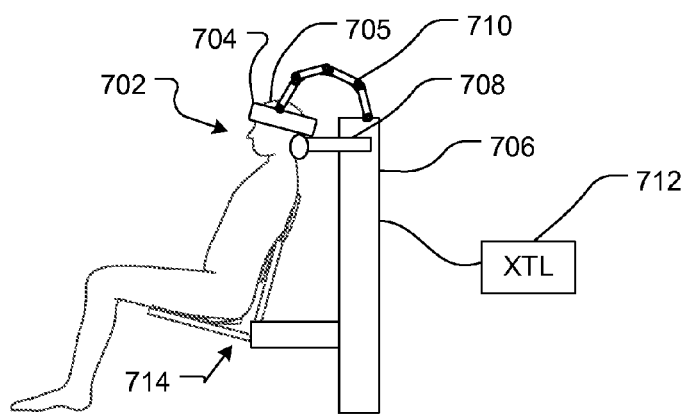
FIG. 7 illustrates an alternative support system according to embodiments of the disclosed subject matter.

Referring to FIG. 7, a support for a stimulating coil 704 is illustrated. A support 706 has a body support 714, in the illustrated example, a seat 714 and a headrest 708 which help to locate and restrain the body of a patient or subject. The headrest 708 may provide a restraining element such as a clamp or belt that wraps around the head of the user. Alternative head restraints may be used as well. A support arm 710 locates the stimulating coil 704 and supports it in a desired position relative to the head 705 of the subject or patient 702. The stimulating coil is attached to a controller 712 which may be mechanically integrated with the support 706.

Figure 8:
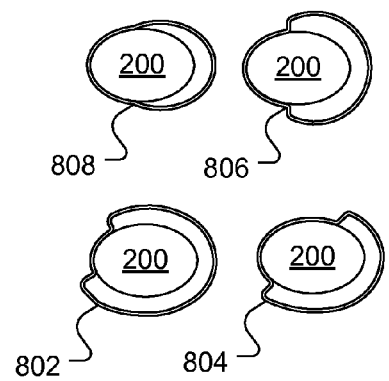
FIG. 8 illustrates various crown coil embodiments with close conforming and non-conforming portions according to embodiments of the disclosed subject matter.

Referring to FIG. 8, several embodiments of a solenoid wound crown coil are illustrated to show variations of how such a coil may have a portion that lies in contact with or close to the skin and portion that is relatively remote from the skin. Embodiments 808 and 605 conform to the skull 200 and lie close to the skin in a front part of the head 200 and remote in a rear part of the head. The latter two coils 806 and 808 may also represent coils in which the conforming part is located at the rear of the head. Embodiments 802 and 804 are coils which lie close to relatively small parts of the head and illustrate that the conforming and non-conforming parts need not be symmetric. Other variations are possible in order to target desired regions of the head or other tissue structure as will be evident to those of skill in the art.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

What is claimed is:

1. A tissue stimulator, comprising:
a pulse generator configured to generate one or a train of pulses of at least 1000 volts at a current of at least 1000 amperes in an insulated winding of multiple turns;
the insulated winding of multiple turns having a central vertical axis and being electrically connected to the pulse generator;
the winding having an opening which has a maximum size, and being configured to wrap around a patient's head with the axis passing vertically and centrally through the head;
the winding being an air core winding having a series of turns forming a solenoid,
wherein the turns at a first side of the axis are closer to the central axis than the turns at a second side of the axis such that when positioned on the patient's head, the turns at the first side are positioned closer to the skin than the turns at the second side, the turns at the first side forming an anatomically conforming portion of the winding around a first portion of the head, and the turns at the second side forming an anatomically conforming portion of the winding around a second portion of the head,
the winding having a dimension along the axis that is at least one third of the maximum size of the opening.

2. The stimulator of claim 1, further comprising a support attached to the winding, the support having an engagement portion for the patient's body or the patient's head and further being adapted for positioning the winding relative to the patient's body or head.

3. The stimulator of claim 2, wherein the support includes a support device that is wearable on the head as a crown, a body restraint, and a positioning arm supporting the winding.

4. A method of stimulating tissue of a living patient, comprising:
surrounding a body part of the patient with a conductive multi-turn winding forming a coil that encircles the body part in such a way as to have the coil be positioned closer to the body part in one location than from the body part at another, radially opposite location, the winding having an axial dimension that is substantially greater than a radial thickness:
passing current pulses of at least 1000 amperes through the winding to generate magnetic field pulses and thereby generate deep tissue electric field pulses within the tissue of the body part,
wherein the body part is the patient's head, and the current and pulse shape are sufficient to generate a peak electrical field magnitude of 1 V/cm at a depth of 4 cm.

5. The method of claim 4, wherein the coil has an approximately circular cross section with an inside opening having a maximum dimension of at least 8 cm and an axial dimension of at least 4 cm.

6. The method of claim 4, wherein the coil includes an insulated coil.

7. The method of claim 4, wherein the surrounding includes positioning the winding over the body part, wherein the axial dimension of the winding is greater on a first radial side of the winding than a second, radially opposite side, whereby an intensity of the electrical field generated in the tissue of the body part proximate the second side, whose turns are effectively fanned out relative to the first side, is less than an intensity of the electrical field generated in the tissue of the body part proximate the first side upon the passing.

8. The method of claim 4,
wherein the tissue is a tissue of a brain, the winding is an air coil winding, and the body part is the patient's head; and
wherein the surrounding includes:
surrounding the brain with the air coil winding forming a solenoid and energizing the solenoid to generate an electrical field whose peak intensity within the brain at 4 cm depth is 1 V/cm by generating a magnetic field which produces an electrical field whose peak intensity, within the brain at a depth of less than 0.3 cm, is less than 3 V/cm, the surrounding including placing at least a portion of the solenoid in direct contact with the skin of the patient's head.

9. A tissue stimulator, comprising:
a support mechanism in a shape of a wearable helmet adapted to support an air core winding with an internal diameter suitable for fitting over an adult human head as a crown with an approximately cylindrical shape and an axial dimension of about ⅓ of the internal diameter;
the winding being capable of handling a peak current of over 1000 amperes and insulated for a voltage of a least 1000 volts, to generate an electrical field whose peak intensity within the brain at 4 cm depth is 1 V/cm, and
wherein the support mechanism is adapted to be worn on the head such that a central vertical axis of the winding passes vertically through the center of the head, the support mechanism including adjustable spacers attached to the support mechanism to position the winding around the head so that the winding along a frontal portion of the head is closer to the skin than the winding along an occipital portion of the head.

10. The stimulator of claim 9, further comprising a pulse generator configured to generate one or a train of pulses of at least 1000 volts at a current of at least 1000 amperes with frequency components above 100 Hz.

11. A tissue stimulator, comprising:
a solenoid device sized and shaped to surround a body part and having a wall with a thickness, an axial dimension, and an opening with a maximum opening dimension;
wherein the axial dimension of the solenoid is along an axis that passes vertically through the opening and centrally through the body part;
the axial dimension being substantially greater than the wall thickness,
at least a portion of the wall being shaped to conform to a shape of the body part,
the solenoid including a multi-turn insulated coil that encircles the body part;
an energization device configured to pass current pulses of at least 1000 amperes through the coil to generate magnetic field pulses and thereby generate deep tissue electrical field pulses within the tissue of the body part,
wherein the coil turns positioned on a first side of the axis are closer to a skin of the body part than the coil turns positioned on a second side of the axis,
wherein the axial dimension of the solenoid on the second side of the axis is greater than the axial dimension of the solenoid on the first side of the axis,
wherein the coil turns positioned on the second side are effectively fanned out relative to the first side, whereby, upon passing, an intensity of the electrical field generated in the tissue of the body part proximate the second side is less than an intensity of the electrical field generated in the tissue of the body part proximate the first side.

12. The stimulator of claim 11, wherein the body part is a human head and the current and pulse shape are sufficient to generate a peak electrical field magnitude of 1 V/cm at a depth of 4 cm.

13. The stimulator of claim 11, wherein the solenoid has an approximately circular cross section with the opening having a maximum dimension of at least 8 cm and the axial dimension of at least 4 cm.

14. The stimulator of claim 11, wherein the solenoid axial dimension is at least ⅓ of the maximum opening dimension.

15. The stimulator of claim 11, wherein the body part is a head of a patient, the stimulator further comprising a support adapted to support the solenoid on the head as a crown.

16. The stimulator of claim 15, further comprising a set of spacers to permit the support to be positioned such that only a selected portion of the solenoid is adjacent the skin.

* * * * *